United States Patent [19]

Bauman

[11] Patent Number: 4,583,528
[45] Date of Patent: Apr. 22, 1986

[54] EXAMINING DEVICE WITH IMPROVED OPTICAL COUPLING BETWEEN THE LIGHT SOURCE AND LIGHT CONDUCTOR

[76] Inventor: Jack Bauman, 1677 San Onofre Dr., Pacific Palisades, Calif. 90272

[21] Appl. No.: 669,474

[22] Filed: Nov. 8, 1984

[51] Int. Cl.[4] ............................ A61B 1/06; F41M 3/04
[52] U.S. Cl. ....................... 128/11; 362/296; 362/347; 362/804
[58] Field of Search ............... 128/11, 10, 4, 6; 362/109, 119, 120, 296, 341, 347, 350, 804

[56] References Cited

U.S. PATENT DOCUMENTS

| 3,426,749 | 2/1969 | Jephcott | 128/11 |
|---|---|---|---|
| 3,598,113 | 8/1971 | Moore | 128/11 |
| 3,609,340 | 9/1971 | Habro | 362/347 X |
| 3,766,909 | 10/1973 | Ozbey | 128/11 |
| 3,771,514 | 11/1973 | Huffman et al. | 128/11 |
| 3,826,248 | 7/1974 | Gobels | 128/11 |
| 4,037,588 | 7/1977 | Heckele | 128/11 |
| 4,114,609 | 9/1977 | Moses | 128/11 |
| 4,273,112 | 6/1981 | Heine et al. | 128/11 |
| 4,295,465 | 10/1981 | Racz et al. | 128/11 |
| 4,306,547 | 12/1981 | Lowell | 128/11 |
| 4,320,745 | 3/1982 | Bhitiyakul et al. | 128/11 |

Primary Examiner—William H. Grieb
Attorney, Agent, or Firm—Fulwider, Patton, Rieber, Lee & Utecht

[57] ABSTRACT

An examining or viewing device such as a laryngoscope having improved optical coupling between a light source and a light receiving face of a light conductor. The light source is provided with a reflector preferably ellipsoidal in shape which concentrates the light reflected into a converging conically shaped light beam which fall essentially in its entirety onto the light receiving surface of the light conductor.

11 Claims, 6 Drawing Figures

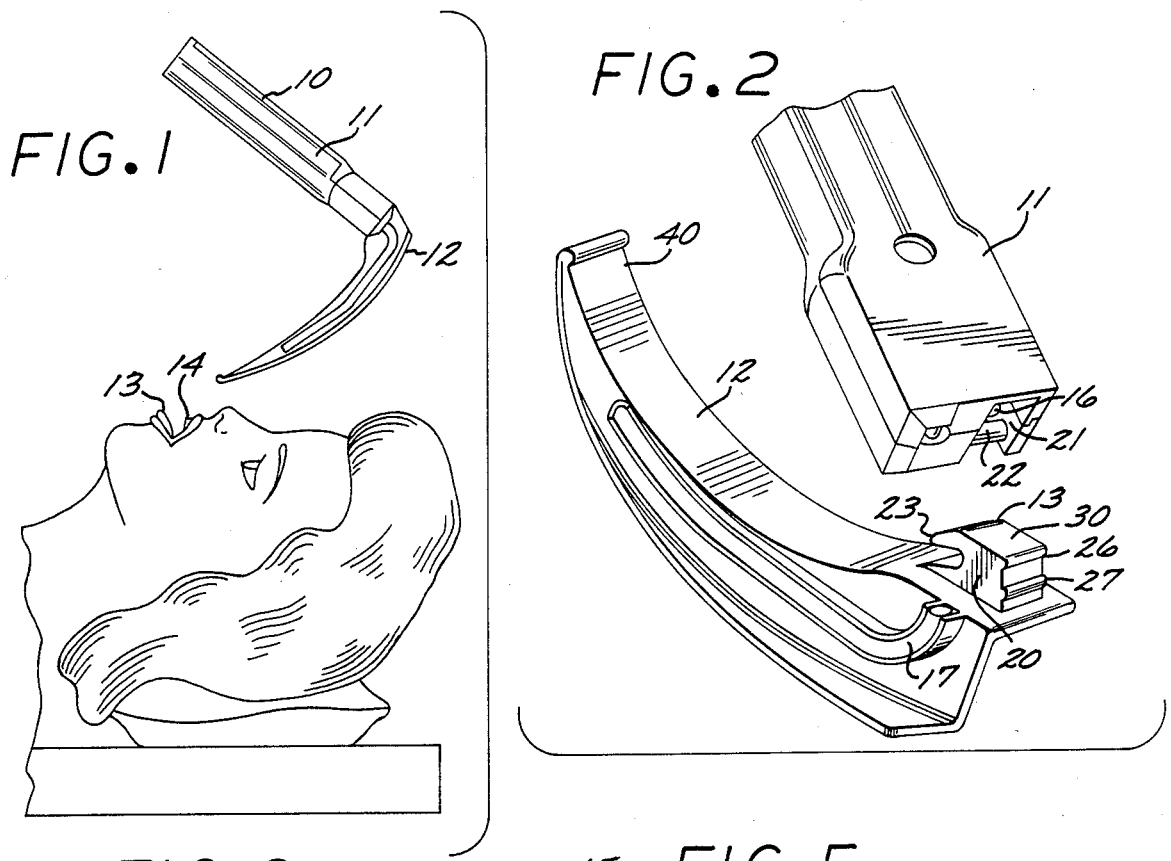
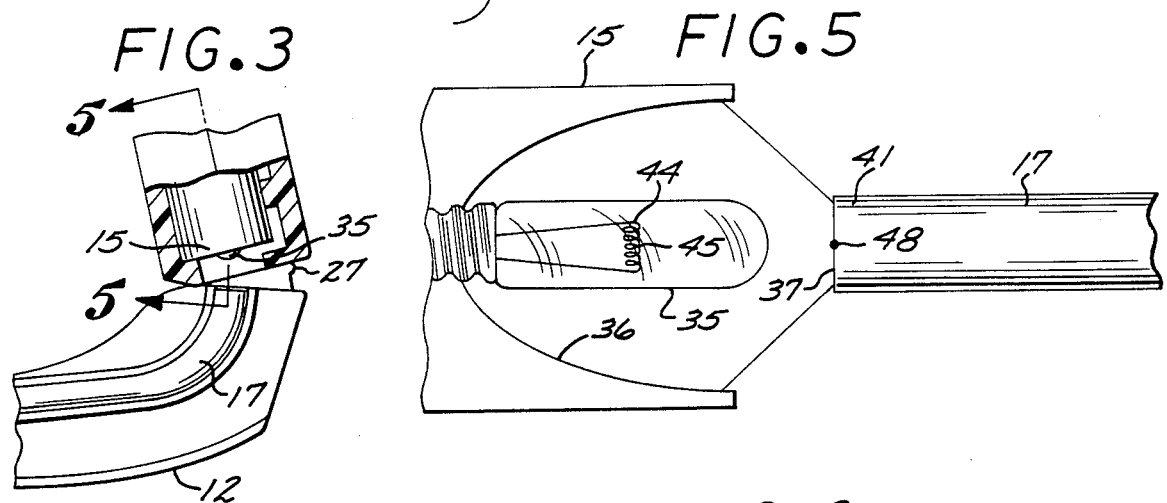
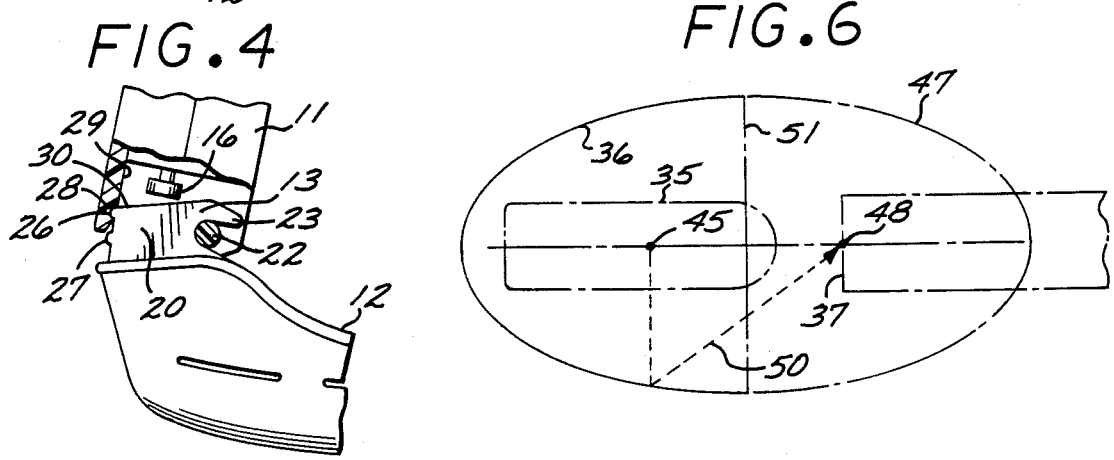

EXAMINING DEVICE WITH IMPROVED OPTICAL COUPLING BETWEEN THE LIGHT SOURCE AND LIGHT CONDUCTOR

BACKGROUND OF THE INVENTION

This invention generally relates to examining reviewing devices such as laryngoscopes, and particularly to an improved system to optically couple a light source in the handle thereof to a light conductor in the blade which supplies light to the field of view.

Laryngoscopes generally comprise a blade and a cooperating handle which are connected together in an L-shaped configuration. The handle normally serves as an enclosure for one or more batteries which energize a light source in the top of the handle. The switch for energizing the light source is usually positioned at the top of the handle, immediately adjacent to the light source and is activated by the blade when it is connected to the handle. Light from the light source is directed to the proximal end of a light conductor disposed in or on the blade. Light passes through the light conductor to the distal end thereof to illuminate field of view such as the patient's mouth and larynx during the examination thereof by medical personnel.

When using the device, the surface on the blade adjacent to the handle is used to press against the tongue and mandible of a patient in a supine position in order to prevent the patient's tongue from obstructing the view during visual examination of the larynx. The opposite blade surface is positioned opposing the upper front teeth of the patient which are occasionally used as a fulcrum to expose the larynx. While the instrument is useful in examining the larynx, the primary function of the laryngoscope is to expose the larynx in order to facilitate the insertion of an endotracheal tube into the trachea of the lungs to administer anesthetic gases.

In the prior examining devices, the light generated by the light source was not properly directed to the light receiving end of the light conductor so, that consequently, much of the light was lost either by being absorbed by the interior of the handle or by light rays which were scattered by the light source or reflector and which did not land on the receiving face of the light conductor. This poor optical coupling of the light source to the light conductor was not only an inefficient use of light, but the scattered or stray light rays tend to be distracting during the examination procedures and they tend to build up much heat.

While there has been a need to provide improved optical coupling between the light source and the light conductor in laryngoscopes and other examining devices, little improvement has been made in this particular area. The present invention provides an improved means to optically couple the light source in the handle to the light conductor associated with the blade, thereby resolving many of the aforesaid problems of the prior devices.

SUMMARY OF THE INVENTION

The present invention is directed to an improved system for optically coupling a light source to a light conductor in an examining device, such as a laryngoscope, and particularly to an improved reflector which concentrates the light emitted from the light source onto the light receiving face on the proximal end of the light conductor.

In accordance with the present invention, the light source in the handle of the examining device is provided with an improved reflector for concentrating the light emitted from the light source onto the light receiving surface of the light conductor. The reflector is shaped and sized to concentrate the light into a converging, conically shaped light beam which is small enough so that essentially all of the conically shaped light impacts the light receiving face of the light conductor. By concentrating the light on the receiving face of the light conductor in this manner, not only is the amount of light directed to the field of view substantially increased, but the amount of distracting scattered or stray light from the light source is substantially reduced.

The shape of the reflector is generally ellipsoidal in nature and the particular dimensions of the reflector depends for the most part on the size and nature of the light bulb utilized in the light source, the size and shape of the light receiving surface on the light conductor and the distance between the light receiving face of the conductor and the light source. The filament in the light source should be at the focal point of the ellipsoid within the reflector and the light receiving face of the light conductor should be at the other focal point of the ellipsoid outside the reflector. Generally, the ratio of the major to minor axis of the ellipsoid should range from about 1.2 to 3.0.

The light source, usually battery powered, is provided in the top of the handle of the examining device. A switch for energizing the light source is also preferably positioned on the top of the handle so that it can be actuated when the blade is fixed in an operative position on the handle. A light conductor is provided in or on the blade for transferring light from the light source to the distal end of the blade where it illuminates the field of view when the laryngoscope or other examining device is in use. The light receiving face at the proximal end of the light conductor should be essentially perpendicular to the axis of the conical light beam and should be positioned adjacent to the light source at or close to the focal point of the ellipsoid to capture as much of the light as possible.

Preferably, the examining device or laryngoscope is designed as described in co-pending application Ser. No. 633,633, filed on July 23, 1984, by the present inventor, so that the blade can be fixed in a ready position on the handle without activating the light switch and then moved into an operative position which activates the light switch and positions the light receiving face of the conductor adjacent to light source in the prescribed manner.

The present invention provides an improved light coupling means, suitable for use in an examining device such as a laryngoscope, which greatly increases the light directed to the field of view for a given power source and greatly decreases the distracting scattered or stray light lost between the light source and the light conductor and an undesirable heat build-up. In the alternative, the present invention provides substantially reduced power requirements for a given light level.

These and other features and advantages of the invention will become more apparent from the following detailed description when taken in conjunction with the accompanying drawings.

BRIEF DESCRIPTION OF THE DRAWINGS

FIG. 1 is a side elevational view of the laryngoscope preparatory to being used on a patient;

FIG. 2 is a perspective exploded view of the blade and handle of the laryngoscope shown in FIG. 1;

FIG. 3 is a side elevational view partially in section of the laryngoscope which embodies features of the invention;

FIG. 4 is a side elevational view partially in section of the laryngoscope on the opposite side to that shown in FIG. 3;

FIG. 5 is a cross sectional view of the light source which illustrates the shape of the reflector surface of the light source and the optical coupling thereof with the light conductor; and FIG. 6 is a diagramatic view of that shown in FIG. 5 illustrating the relationship of the reflector shape and the positioning of the light conductor.

DETAILED DESCRIPTION OF THE INVENTION

Reference is made to the drawing which illustrate a laryngoscope embodying features of the present invention. As shown in FIG. 1, the laryngoscope 10, which comprises a handle 11 and detachable blade 12, is utilized to press the patient's tongue and mandible 13. The patient's front teeth 14 are frequently used as a fulcrum for the blade 12 in order to more completely expose the patients's larynx during the examination thereof.

In general, as shown in FIGS. 2–4, the laryngoscope 10 comprises a handle 11, a detachable blade 12, means 13 to detachably secure the blade 12 to the handle 11 in a general L-shaped configuration, a light source 15 and a light switch 16 to energize the light source in the handle and a light conductor 17 in the blade 12. The blade 12 is attached to the handle 11 in a pivotal fashion wherein connection means 13 comprises an appendage 20 of the blade 12 is inserted into the open top channel 21 of the handle 11 with pivotal motion so that the front end 23 of the appendage 20 is hooked under the pivot rod 22 provided in the channel 21. Detents 26 and 27 engage a groove 28 in the back surface wall 29 of the channel 21 to urge the appendage 20 into a more firm engagement with the pivot rod 22 and to thereby fix the blade 12 with respect to the handle 11. When the blade 12 is in operating position as shown in FIG. 3, the surface 30 of the appendage 20 engages a light switch 16 thereby activating it so that the light source 15 is energized by suitable power source such as batteries (not shown) provided in the handle 11.

The particular embodiment shown is designed to be formed from plastic materials which lessen considerably the cost for such devices over prior metal devices. Moreover, the plastic blade is intended to be disposable.

FIGS. 5 and 6 illustrate optical coupling in accordance with the invention between the light source 15 and the light conductor 17. The light source 15 includes a light bulb 35 with a reflector 36 which preferably has an ellipsoidal shape as shown in the drawings. The reflector 36 concentrates the light from the light bulb 35 onto the light receiving surface 37 of the light conductor 17. The conductor 17 is positioned on the blade 12 and adapted to transmit the light to the distal end 40 of the blade 12 wherein it illuminates field of view such as the patient's mouth and larynx during the examination thereof with the examining device 10.

As best shown in FIGS. 5 and 6, the filament 44 of the bulb 35 is positioned at or very close to the focal point 45 which lies within the reflector 36 and on the longitudinal or major axis 46 of the ellipsoid shaped reflector 36. The ellipsoidal shape 47 of the reflector 36 concentrates the reflected light into a converging, conically shaped light beam 49 with a point of convergence at or about the focal point 48 of the ellipsoid shape 47 outside the reflector 36. An individual light beam 50 is shown in FIG. 6. The light receiving face 37 is positioned at or very close to the focal point 48 of the ellipsoid shape to capture as much light as possible. Because the light receiving face 37 has an area (i.e., it is not a point) it may be centrally placed along the major axis 46 forward or behind the focal point 48 and still capture essentially all of the conically shaped light beam 49. In general, the ratio of the major axis 46 to the minor axis 51 of the ellipsoid shape 47 should range from about 1.1 to about 3.

By concentrating the light in the manner described, onto the light receiving surface 37 of the light conductor 17, substantially more of the light is then transmitted to the distal end 40 of the blade 12 which thereby brightens the observation field. The light receiving face 37 at the proximal end 41 of the conductor 17 should be positioned as close as possible to the focal point 48 of the ellipsoid shape 47 to ensure capture of as much as possible of the light beam concentrated by the reflector 36.

The light conductor 17 may be formed from conventional light conducting materials such as glass or clear plastics. Many of the light conductors previously used provided an uneven light pattern to the field of view which would mask the natural color density gradiations of the matter being examined. To avoid this problem, the exit face of the light conductor 17 is preferably roughened or frosted, for example, by roughening the surface of the die cavity which shapes the discharged end of the conductor 17 by sand blasting which provides a relatively uniform light density across the field of view thereof. Thus in this manner a brighter and more uniform lighting of the field of view is obtained. Other methods of roughening the discharge surface of conductor 17 include rubbing the discharge surface with an abrasive or chemical etching the discharge surface.

Although the specific embodiment of the invention is described herein in connection with laryngoscopes, it is obvious that the improved means to optically couple the light source and the light conductor can be employed in other devices. Moreover, modifications and improvements can be made to the present invention without departing from the inventive concepts thereof.

I claim:

1. In an examining or viewing device having a light source and a light conductor to conduct light away from the light source to a field of view, the improvement in the optical coupling of the light source to the light conductor comprising, a reflector associated with the light source which is shaped to reflect light from the light source into a converging, conically shaped light beam and the light conductor having a light receiving face which is positioned sufficiently close to the point of convergence of the conically shaped light beam to receive essentially all of the light beam.

2. The device of claim 1 wherein the reflector has an essentially ellipsoid shape with two focal points, one within the reflector and one outside of the reflector.

3. The device of claim 2 wherein the light source is provided with a filament which lies within the reflector at or about the focal point of the ellipsoid shape formed by the reflector along the longitudinal axis thereof and the light receiving face of the light conductor is positioned sufficiently close to the focal point of the ellipsoid shape outside of the reflector where the light beam converges to capture essentially all of the conically shaped light beam.

4. The device of claim 3 wherein the ellipsoid shape has a major axis and a minor axis and the ratio of the major to the minor axes of the ellipsoid shape ranges from about 1.1 to about 3.

5. In a laryngoscope comprising a blade, a handle, means to detachably secure the blade to the handle in an L-shaped configuration, a light source in the handle optically coupled to a light conductor associated with the blade to direct light from the light source to the field of view of the laryngoscope, the improvement in the optical coupling of the light source to the light conductor comprising, a reflector associated with the light source which is shaped to reflect light from the light source into a converging conically shaped light beam and the light conductor having a light receiving face which is positioned sufficiently close to the point of convergence of the conically shaped light beam to receive essentially all of the light beam.

6. The laryngoscope of claim 5 wherein the reflector is ellipsoidal in shape with two focal points, one within the reflector and one outside of the reflector.

7. The laryngoscope of claim 6 wherein the light source has a filament which lies within the reflector at or about the focal point of the ellipsoid shape formed by the reflector.

8. The laryngoscope of claim 7 wherein the light receiving face of the light conductor is positioned sufficiently close to the focal point outside of the reflector along the longitudinal axis thereof to capture essentially all of the conically shaped light beam when the blade is in operating position.

9. The laryngoscope of claim 6 wherein the ellipsoid shape has a major and a minor axis and the ratio of the major to minor axes of the ellipsoid shape ranges from about 1.1 to about 3.

10. The laryngoscope of claim 5 wherein the light receiving face is perpendicular to the axis of the conically shaped light beam.

11. The laryngoscope of claim 5 wherein the light conductor has a light discharge face at the distal end thereof which is roughened or frosted to produce a diffused light with relatively uniform light beam density.

* * * * *